United States Patent [19]

Yuan et al.

[11] Patent Number: 5,342,361
[45] Date of Patent: Aug. 30, 1994

[54] DUAL TIER SPINAL LOCKING AND RETRIEVING SYSTEM AND INSTRUMENTATION FOR ADMINISTERING SUCH SYSTEM PERCUTANEOUSLY

[76] Inventors: Hansen A. Yuan, 5066 Pine Valley Dr., Fayetteville, N.Y. 13066; Chih-I Lin, 813 S. Golden Pardos Dr., Diamond Bar, Calif. 10765

[21] Appl. No.: 4,608

[22] Filed: Jan. 14, 1993

[51] Int. Cl.$^5$ ............................................. A61F 5/04
[52] U.S. Cl. ................................. 606/61; 606/60; 606/72; 606/73
[58] Field of Search ............... 606/60, 61, 69, 70, 606/71, 72, 73; 623/17

[56] References Cited

U.S. PATENT DOCUMENTS

| | | | |
|---|---|---|---|
| 4,653,481 | 3/1987 | Howland et al. | 606/61 |
| 4,763,644 | 8/1988 | Webb | 606/61 |
| 5,030,220 | 7/1991 | Howland | 606/61 |
| 5,084,048 | 1/1992 | Jacob et al. | 606/61 |
| 5,092,867 | 3/1992 | Harms et al. | 606/61 |
| 5,127,912 | 7/1992 | Ray et al. | 606/61 |
| 5,129,899 | 7/1992 | Small et al. | 606/71 |
| 5,147,360 | 9/1992 | Dubousset | 606/61 |
| 5,176,679 | 1/1993 | Lin | 606/61 |
| 5,196,014 | 3/1993 | Lin | 606/72 |

FOREIGN PATENT DOCUMENTS 1623636  1/1991  U.S.S.R. ............................ 606/61

Primary Examiner—David Isabella
Assistant Examiner—Debra S. Brittingham
Attorney, Agent, or Firm—Bacon & Thomas

[57] ABSTRACT

A dual-tier spinal locking and retrieving system comprises a plurality of spinal pins, one or more lower auxiliary locking members, a plurality of connecting members, one or more upper auxiliary locking members, and a plurality of locking devices. Each of the spinal pins is provided with a fastening portion, a stop portion and a first receiving portion. The lower auxiliary locking members are used to brace or tighten the first receiving portion of the spinal pin so as to establish a lower auxiliary locking framework. The connecting member is provided with a second receiving portion and a third receiving portion. Ther upper auxiliary locking members are used to brace or tighten the third receiving portion of the connecting member so as to established an upper auxiliary locking framework. The locking devices are used to construct a dual-tier spinal locking and retrieving system for which a percutaneous instrumentation is provided.

9 Claims, 3 Drawing Sheets

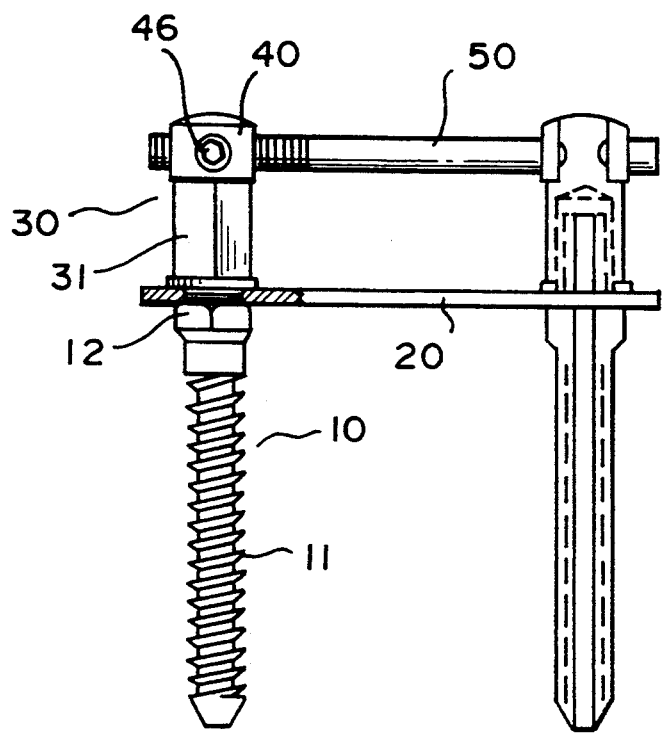
FIG. 3-a
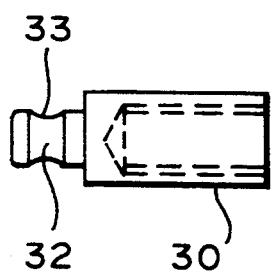
FIG.3-b
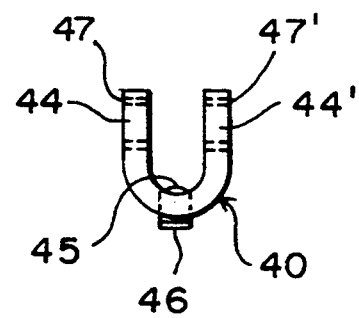
FIG.3-c
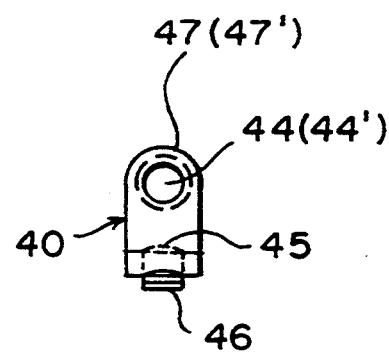
FIG.3-d

DUAL TIER SPINAL LOCKING AND RETRIEVING SYSTEM AND INSTRUMENTATION FOR ADMINISTERING SUCH SYSTEM PERCUTANEOUSLY

BACKGROUND OF THE INVENTION

The present invention relates to a dual-tier spinal locking and retrieving system and an instrumentation for administering such system percutaneously.

In general, the conventional method of administering a spinal locking and retrieving system involves an anterior surgical incision or a lateral surgical incision. Such a surgical incision is generally so large as to facilitate an implantation of the spinal locking and retrieving system, thereby subjecting a patient receiving the treatment to an excessive bleeding, a painfully slow recuperation, and a bacterial infection. With a view to overcoming the shortcomings of the spinal locking and retrieving system of the prior art, this inventor disclosed an improved spinal locking an retrieving system in U.S. Pat.No. 5,176,679 nevertheless this inventor's new system still requires a surgeon to make a large incision so as to implant the system.

SUMMARY OF THE INVENTION

It is therefore the primary objective of the present invention to provide a spinal locking and retrieving system, which can be implanted percutaneously.

It is another objective of the present invention to provide a dual-tier spinal locking and retrieving system.

It is still another objective of the present invention to provide a dual-tier spinal locking and retrieving system, which can be implanted percutaneously.

It is still another objective of the present invention to provide an instrumentation for administering a percutaneous implantation of a spinal locking and retrieving system.

It is still another objective of the present invention to provide an instrumentation for administering an implantation of a dual-tier spinal locking and retrieving system.

It is still another objective of the present invention to provide an instrumentation for administering a percutaneous implantation of a dual-tier spinal locking and retrieving system.

In keeping with the principles of the present invention, the foregoing objectives of the present invention are attained by a dual-tier spinal locking and retrieving system, which can be implanted percutaneously in the back of a patient and which comprises the structures described below.

Each of a plurality of spinal pins has a lower portion serving as a fastening portion, a middle portion acting as a stop portion, and an upper portion forming a first receiving portion. The fastening portion is inserted with a screwlike motion into a vertebra to be fastened securely, with the stop portion serving to prevent the spinal pin from penetrating further into the vertebra. The first receiving portion is threaded evenly around its outer surface. Among the spinal pins mentioned above, there are at least two spinal pins which have the first receiving portion provided with a lower auxiliary locking mount.

One or more lower auxiliary locking members are used to brace or tighten the lower auxiliary locking mounts of the first receiving portions of the spinal pins described above.

Each of a plurality of connecting members has a lower portion forming a second receiving portion and an upper portion serving as a third receiving portion. The second receiving portion has a threaded hole so dimensioned as to engage the first receiving portion of the spinal pin and to clamp securely the lower auxiliary member. Among the connecting members mentioned above, there are at least two connecting members which have the third receiving portion provided with an upper auxiliary locking mount.

One or more upper auxiliary locking members are used to brace or tighten the upper auxiliary locking mounts of the third receiving portions of the connecting members described above.

Each of a plurality of locking devices is used to hold securely the third receiving portion of the connecting member.

The present invention is characterized in that it includes lower auxiliary locking members and upper auxiliary locking members by which a dual-tier auxiliary locking is accomplished, and that it can be implanted percutaneously to lock and retrieve a deformed vertebra of a patient without subjecting the patient to an excessive bleeding and a bacterial infection.

The foregoing objectives, structures and functions of the present invention will be better understood by studying the following detailed description of preferred embodiments of the present invention in conjunction with the drawings provided herein.

BRIEF DESCRIPTION OF THE DRAWINGS

FIG. 1-*a* is a side elevational view of a connecting member 30 having a threaded hole indicated by dotted lines, according to the present invention as shown in FIG. 1.

FIGS. 3-*a* through 3-*d* show schematic views of another preferred embodiment of the present invention.

DETAILED DESCRIPTION OF THE PREFERRED EMBODIMENTS

Figure 1:
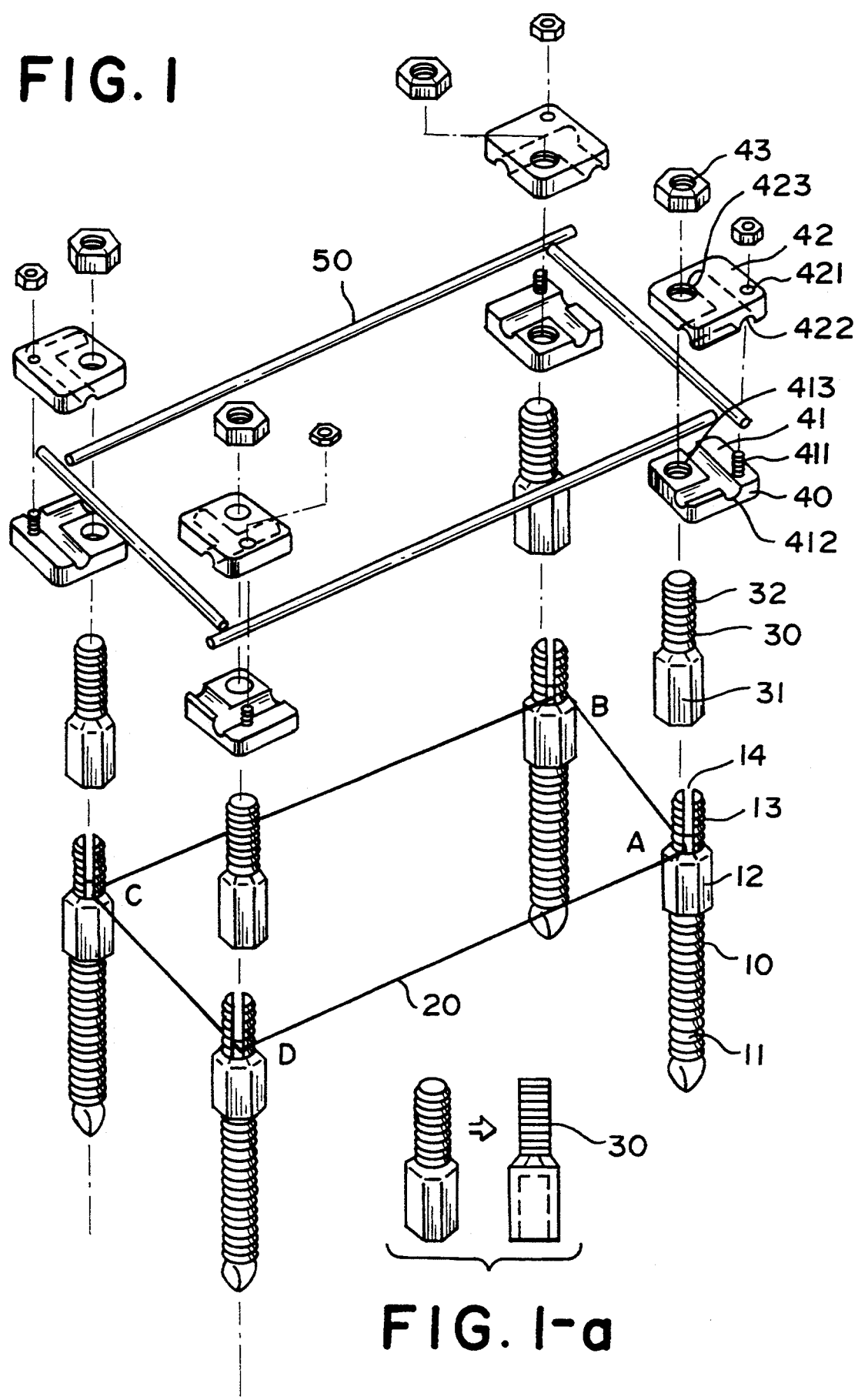
FIG. 1 shows an exploded view of a preferred embodiment of the present invention.
Figure 2:
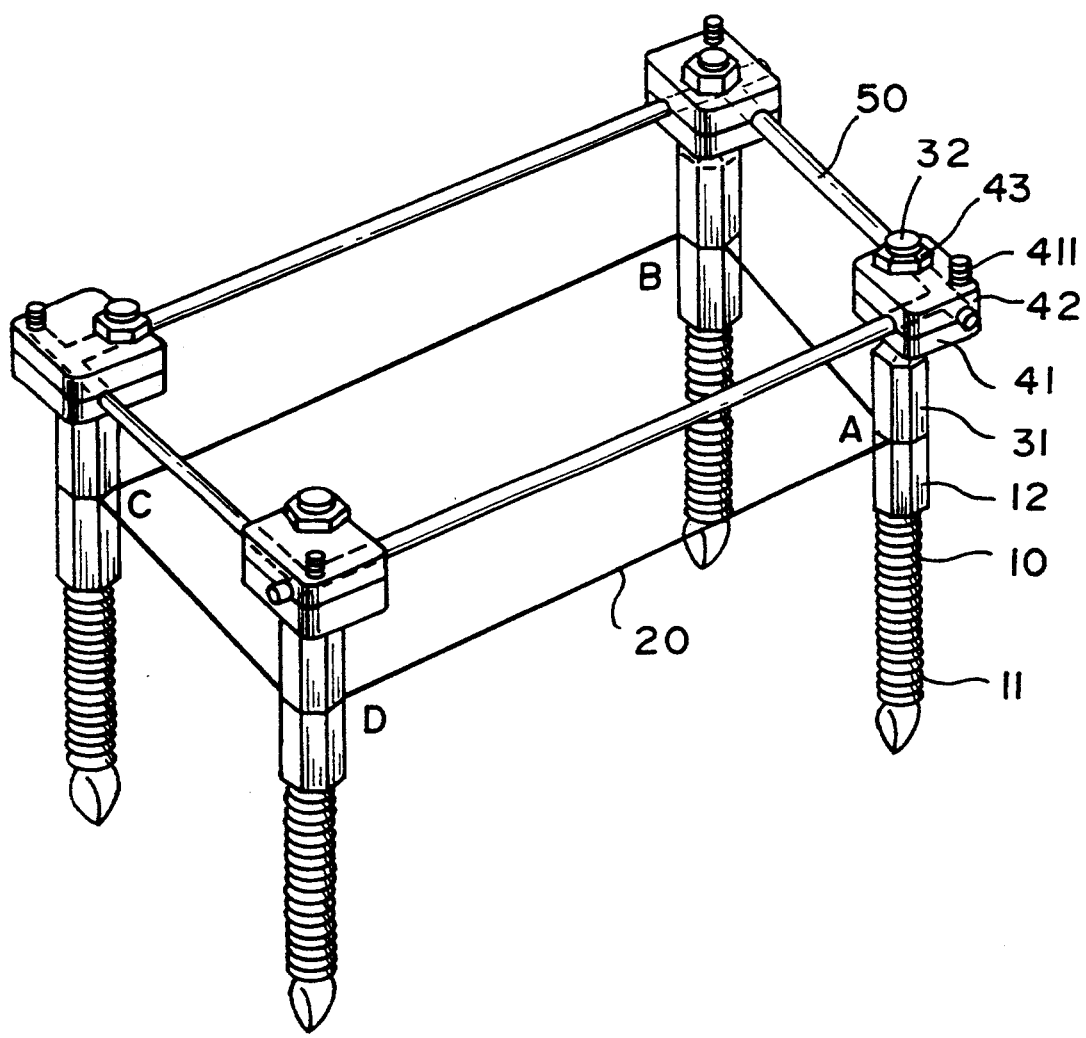
FIG. 2 shows the preferred embodiment in combination, according to the present invention as shown in FIG. 1.

Referring to FIG. 1, a spinal pin 10 of the present invention is shown to comprise a fastening portion 11, a stop portion 12, a first receiving portion 13, and an auxiliary locking mount 14. There are lower auxiliary locking members 20, connecting members 30, second receiving portions 31 and third receiving portions 32 of the connecting members 30. A locking device 40 is composed of a lower clamp piece 41, an upper clamp piece 42 and a nut 43. The lower clamp piece 41 is provided with a locking screw 411, a locking groove 412 and a through hole 413. The upper clamp piece 42 is provided with a locking hole 421, a locking groove 422 and a through hole 423. An upper auxiliary locking member 50 is of a rod-shaped construction.

The first receiving portion 13 is of a screwlike construction while the second receiving portion 31 is of a nutlike construction, or vice versa. The third receiving portion 32 may be similar in construction to the first receiving portion 13 having an evenly threaded outer surface. The upper auxiliary locking member 50 may be so modified as to work as an auxiliary locking cable.

The locking device 40 is in fact a unitary piece of a nutlike construction.

As shown in FIG. 1, the lower auxiliary locking members 20 are fitted respectively into the points A, B, C and D, so as to form a lower tier locking of a quadrangular shape. The lower tier locking may be constructed by mounting the lower auxiliary locking members 20 on one or more places between AB, AC, AD, BC, BD, or CD, preferably on more than one place so as to hold the lower tier locking securely in place. Similarly, an upper tier locking may be constructed in other specific shapes which are different from the quadrangular shape shown in FIG. 1.

Referring to FIG. 1 again there is a dual-tier spinal locking and retrieving system of the present invention. In the process of administering a percutaneous implantation of the system of the present invention, four spinal pins 10 are implanted percutaneously into two vertebrae to be fastened. The two vertebrae are not shown in FIG. 1. The lower auxiliary locking members 20 are fitted respectively, in a sequential order of A, B, C, D, and back to A, into slits made by the four spinal pins 10. Thereafter, four connecting members 30 are coupled respectively with the four spinal pins 10. With the exception of the connecting member 30 located at point A, the connecting members 30 should not be fastened. Use surgical tools to clamp securely the two spinal pins 10 located respectively at points A and B so as to shorten the gap between A and B. The connecting member 30 located at point B is then fastened securely before the surgical tool holding the spinal pin 10 located at point B is removed. Similarly, the connecting members 30 located repectively at points C and D are fastened securely to the spinal pins 10. Four lower clamp pieces 41 are fitted respectively over the four connecting members 30 while four upper auxiliary locking members 50 are mounted respectively in the four locking grooves 412 of the four lower clamp pieces 41, which are then united respectively with four upper clamp pieces 42 in such a manner that the upper auxiliary locking members 50 are received respectively in the locking grooves 42 of the four upper clamp pieces 42. With the exception of the locking nut 43 located at point A, other locking nuts 43 are not fastened. Use the surgical tools to force the connecting members 30 to move outwards so as to widen the gap therebetween before fastening securely the locking nut 43 located at point B. Remove the surgical tools exerting an outward force on the connecting members 30. Similarly, the locking nuts 43 located respectively at points C and D are fastened securely.

In the event that the upper auxiliary locking members 50 take the form of a rod, an inward tightening approach should be employed to construct the upper tier locking. It should be noted that the terms "lower", "middle" and "upper" used throughout this disclosure are only intended to represent relative positions corresponding to the nearest, intermediate and farthest distances from each vertebra respectively.

Prior to administering an implantation of the dual-tier spinal locking and retrieving system of the present invention, a surgeon should remove the deformed portion of the vertebrae by means of an endoscopic sugery or a similar surgery, as suggested in a method disclosed in the U.S. Pat. No. 4,545,374. With the help of a X-ray machine, or a C-arm, or a guide pin, a surgeon can fasten the spinal pins 10 to the vertebrae with precision.

Another preferred embodiments of the present invention is illustrated in FIG. 3-a in which like numerals are used to designate those elements which are corresponding to those of the preferred embodiment as shown in FIG. 1. The third receiving portion 32 and the locking device 40 are so constructed as to form a three-point shear clamp mechanism. As shown in FIG. 3-b, the third receiving portion 32 is of a cylindrical body having a recessed central portion which serves as a shear clamp point of the three-point shear clamp mechanism in order to hold securely the upper auxiliary locking member 50, in conjunction with another two shear clamp points. As shown in FIG. 3-c, the locking device has through holes 44 and 44' for receiving therein the upper auxiliary locking members 50. The locking device 40 is further provided with a threaded hole 45 dimensioned to engage a locking screw 46. The third receiving portion 32 is received in a space formed and defined by the threaded hole 45 and the upper auxiliary locking members 50 passing through the through holes 44 and 44'. When the locking screw 46 is fastened securely, points 47 and 47' urge the upper auxiliary locking members 50, as shown in FIG. 3-c. The points 47 and 47' are among those three points forming the three-point shear clamp mechanism. The FIG. 3-d is a side elevational view of the locking device 40, in which the numerals designating the elements are corresponding to those of FIG. 3-c.

The spinal pins 10, the connecting members 30, the locking device 40, the lower auxiliary locking members 20, and the upper auxiliary locking members 50 are made of biocompatible materials suitable for the orthopedic surgery, such as stainless steel 316 LVM, Ti-6-4, cobalt molybdenum alloy, etc. When the lower auxiliary locking members 20 and/or the upper auxiliary locking members 50 take the form of a cable, they may be made of a material containing the above-mentioned metals or the organic materials suitable for the orthopedic surgery, such as artificial ribbons made of tough carbon fibers or dacron.

The stop portion 12 of the spinal pin 10 has a diameter slightly greater than that of the fastening portion 11. As a result, the stop portion 12 is able to prevent the spinal pin 10 from penetrating into the vertebra beyond the fastening portion 11. In addition, the stop portion 12 also serves to sustain the vertebra. The diameters and the lengths of the fastening portion 11 and the stop portion 12 are dependent on the dimension of the vertebra. The shapes of the fastening portion 11 and the stop portion 12 may be similar to those of the spinal pin of the prior art.

The upper auxiliary locking mount and the lower auxiliary locking mount of the present invention may take the form of a through hole, or a slit, or a central groove, or a lateral groove.

The lower auxiliary locking member of the present invention takes the form of a rod and is made of a soft but substantially nonexpansive wire of single strand, or a soft but substantially nonexpansive cable of multiple strands, or a GRAF band manufactured by a French company called Safir. If the spinal locking and retrieving system of the present invention is intended for use in a percutaneous implantation, the lower auxiliary locking members should preferably take the form of a wire of single strand or a cable of multiple strands. If a partial open surgery is to be administered, a rod-shaped lower auxiliary locking member, or a GRAF band should be used. In case the wire of single strand or the cable of multiple strands is used, the wire or the cable is put through the lower auxiliary locking mounts (such as through holes or slits) of two or more spinal pins before a connecting member is fastened securely thereon. Thereafter, the lower auxiliary locking cable is tightened before another one or more connecting members are fastened securely thereon so that the lower auxiliary locking members hold securely the spinal pins to stabilize the lower tier locking.

According to the present invention, the first receiving portion of the spinal pin, the second receiving portion and the third receiving portion of the connecting member may be so constructed as to take the form of a nut having a threaded hold or of a bolt threaded evenly around its outer surface. It must be noted here that the first receiving portion is of a screwlike receiving portion capable of engaging the second receiving portion of a nutlike construction. The form of the third receiving portion is dependent on the form of the locking device with which the third receiving portion cooperates.

The locking device of the present invention may take the form of a nut, or a bolt, or a clamping means, etc. For example, an ISOLA universal locking system made by Acromed of the United States may be used to cooperate with the third receiving portion to form a three-point shear clamp mechanism.

The upper auxiliary locking members and the lower auxiliary locking members of the present invention are similar in that they may take the form of a rod, or a wire of single stand, or a cable of multiple strands, or a GRAF band, depending on the surgical requirements.

According to the present invention, when the third receiving portion is of a screwlike construction or of a nutlike construction, the auxiliary locking cables may be used as the upper auxiliary locking members. In addition, the locking device should be of a nutlike (or screwlike) construction, so as to enable the upper auxiliary locking members to be held securely between the third receiving portion and the locking device. On the other hand, if the third receiving portion of the connecting member is not of a nutlike (or screwlike) construction, the upper auxiliary locking members may take the form of a rod. In the meantime, the locking device provided with a locking groove should be used to hold the upper auxiliary locking member.

The instrumentation for administering a percutaneous implantation of the dual-tier spinal locking and retrieving system of the present invention comprises the steps described as follows: (1) The fastening portion of the spinal pin is forced completely into the vertebra to be fastened, with the penetration of the spinal pin ceasing at the stop portion of the spinal pin;

(2) At least one lower auxiliary locking member is first put through the auxiliary locking mount of one spinal pin and then through the auxiliary locking mount of another spinal pin via the underside of the muscles adjacent to the vertebra to be fastened;

(3) Arrange the second receiving portions of a plurality of the connecting members on the first receiving portions of the spinal pins, with the second receiving portions remaining unfastened. Fasten the connecting member of the spinal pin, which was first put through the lower auxiliary locking member as referred to in the step (2). Subsequently, this spinal pin and another spinal pin, which was secondly put through the lower auxiliary locking member, are held securely by means of a surgical means so as to keep the gap between the first receiving portions of these two spinal pins slightly smaller than the gap between the fastening portions of these two spinal pins. The connecting member of another spinal pin can be now fastened;

(4) A plurality of the locking devices are caused respectively to engage threadably with the third receiving portions of the connecting members; and (5) In accordance with the methods referred to in steps (2) and (3), fasten the upper auxiliary locking member to the auxiliary locking mount of the third receiving portion of the connecting member, or fasten the upper auxiliary locking member to the locking groove of the locking device.

If necessary, the steps (2), (3) and (5) may be done repeatedly to construct a dual-tier locking framework by means of a plurality of the lower auxiliary locking members and the upper auxiliary locking members. The dual-tier locking framework may be also constructed by means of one lower auxiliary locking member or one upper auxiliary locking member, which is put through the auxiliary locking mounts of a plurality of the spinal pins or the auxiliary mounts of the connecting members.

What is claimed is:

1. A dual-tier spinal locking and retrieving system comprising:
    a plurality of spinal pins, each of said spinal pins including a longitudinally extending lower portion adapted to be fastened into a vertebra, a middle portion having a stop portion which limits the degree to which said lower portion can be fastened within a vertebra and an upper portion defining an externally threaded first receiving portion, the first receiving portion of at least two of said plurality of spinal pins including an opening defining a lower auxiliary locking mount;
    at least one lower auxiliary locking member interconnecting the lower auxiliary locking mounts of said at least two of said plurality of spinal pins;
    a plurality of connecting members, each of said connecting members including a second receiving portion threadably attached to the first receiving portion of a respective one of said plurality of spinal pins with the connecting members attached to said at least two of said plurality of pins securing said at least one lower auxiliary locking member between said at least two of said plurality of spinal pins, each of said connecting members further including a third receiving portion that is longitudinally spaced from said second receiving portion thereof;
    a plurality of clamping units, each of said clamping units being secured to a respective one of said third receiving portions; and
    at least one upper auxiliary locking member extending between the connecting members attached to said at least two of said plurality of spiral pins through respective ones of said plurality of clamping units, said at least one upper auxiliary locking member being longitudinally spaced from said at least one lower auxiliary locking member so as to define a dual-tier locking arrangement.

2. The dual-tier spinal locking and retrieving system according to claim 1, wherein said at least one lower auxiliary locking member is selected from the group consisting of auxiliary locking rods, auxiliary locking wires of single strand, auxiliary locking cables of multiple strands and auxiliary locking bands.

3. The dual-tier spinal locking and retrieving system according to claim 2, wherein the at least one lower auxiliary locking member is selected from the group consisting of auxiliary locking wires of single strand and auxiliary locking cables of multiple strands.

4. The dual-tier spinal locking and retrieving system according to claim 1, wherein said at least one upper auxiliary locking member is selected from the group consisting of auxiliary locking rods, auxiliary locking wires of single strands, auxiliary locking cables of multiple strands and auxiliary locking bands.

5. The dual-tier spinal locking and retrieving system according to claim 4, wherein said at least one upper auxiliary locking member is selected from the group consisting of auxiliary locking rods and auxiliary locking bands.

6. A method of administering a percutaneous implantation of a dual-tier spinal locking and retrieving system comprising:

providing a plurality of spinal pins, each of which includes a longitudinally extending fastening portion, a stop portion and a first receiving portion, and wherein at least two of said plurality of spinal pins are each further provided with an opening defining an auxiliary locking mount;

securing the fastening portion of each of said spinal pins into a respective vertebra with the stop portion thereof remaining outside of the vertebra;

attaching a lower auxiliary locking member between the auxiliary locking mounts of the at least two of said plurality of spiral pins;

providing a plurality of connecting members, each of which includes a second receiving portion adapted to be fastened to the first receiving portion of a respective one of said plurality of spiral pins and a third receiving portion;

fastening one of said plurality of connecting members to the first receiving portion of one of the at least two of said plurality of spinal pins in order to fixedly retain said lower auxiliary locking member;

maintaining a gap between the first receiving portions of the at least two of said plurality of spiral pins slightly smaller than a gap between the fastening portions of the at least two of said plurality of spiral pins while fastening another one of said plurality of connecting members to the other one of the at least two of said plurality of spinal pins in order to fixedly retain said lower auxiliary locking member between the at least two of said plurality of spinal pins;

providing a plurality of clamping units, each of said clamping units being secured to a respective one of the third receiving portions of said plurality of connecting members; and attaching an upper auxiliary locking member between the clamping units on the third receiving portions of the at least two of said plurality of spinal pins with said upper auxiliary locking member being longitudinally spaced from said lower auxiliary locking member.

7. The method according to claim 6, further comprising: selecting from the group consisting of an auxiliary locking wire of single strand and an auxiliary locking cable of multiple strands.

8. The method according to claim 6, further comprising: selecting said upper auxiliary locking member from the group consisting of an auxiliary locking rod, an auxiliary locking wire of single strand, an auxiliary locking cable of multiple strands and an auxiliary locking band.

9. The method according to claim 8, further comprising: selecting said upper auxiliary locking member from the group consisting of an auxiliary locking rod and an auxiliary locking band.

* * * * *